United States Patent
Muñoz et al.

(10) Patent No.: US 10,548,487 B2
(45) Date of Patent: Feb. 4, 2020

(54) WEARABLE VITAL SIGN MONITOR

(71) Applicant: Monovo, LLC

(72) Inventors: Jonathan Muñoz, West Jordan, UT (US); Robert Johnstun, American Fork, UT (US); Steve Taylor, Mill Creek, UT (US)

(73) Assignee: Monovo, LLC, Orem, UT (US)

( * ) Notice: Subject to any disclaimer, the term of this patent is extended or adjusted under 35 U.S.C. 154(b) by 44 days.

(21) Appl. No.: 15/495,759

(22) Filed: Apr. 24, 2017

(65) Prior Publication Data

US 2018/0303419 A1    Oct. 25, 2018

(51) Int. Cl.
| | |
|---|---|
| *A61B 5/021* | (2006.01) |
| *A61B 8/00* | (2006.01) |
| *A61B 5/00* | (2006.01) |
| *A61B 5/0205* | (2006.01) |
| *A61B 5/11* | (2006.01) |
| *A61B 5/024* | (2006.01) |

(52) U.S. Cl.
CPC .......... *A61B 5/021* (2013.01); *A61B 5/0022* (2013.01); *A61B 8/4227* (2013.01); *A61B 5/02055* (2013.01); *A61B 5/02438* (2013.01); *A61B 5/11* (2013.01); *A61B 5/6824* (2013.01); *A61B 5/742* (2013.01); *A61B 5/7405* (2013.01); *A61B 2560/0214* (2013.01); *A61B 2562/0219* (2013.01); *A61B 2562/168* (2013.01)

(58) Field of Classification Search
None
See application file for complete search history.

(56) References Cited

U.S. PATENT DOCUMENTS

| | | | | |
|---|---|---|---|---|
| 5,309,916 A | * | 5/1994 | Hatschek | A61B 5/021 600/452 |
| 7,125,387 B2 | * | 10/2006 | Kawabata | A61N 7/00 601/2 |
| 7,547,282 B2 | * | 6/2009 | Lo | A61B 5/02438 600/437 |

(Continued)

OTHER PUBLICATIONS

International Search Report and Written Opinion for application No. PCT/US18/25883, dated Jun. 28, 2018.

*Primary Examiner* — Carl H Layno
*Assistant Examiner* — Manolis Pahakis
(74) *Attorney, Agent, or Firm* — Workman Nydegger

(57) ABSTRACT

A wearable vital sign monitor. The wearable vital sign monitor includes a band, where the band secures the wearable vital sign monitor relative to a user. The band includes an interior surface, the interior surface being the surface closest to the skin of the user and an exterior surface, the exterior surface opposite the interior surface. The wearable vital sign monitor also includes a first sensor array. The first sensor array is attached to the band and includes at least two sensors. The wearable vital sign monitor further includes a second sensor array. The second sensor array is attached to the band a fixed distance from the first sensor array and includes at least two sensors. The wearable vital sign monitor additionally includes an electronics module. The electronics module is configured to receive a first signal from the first sensor array, receive a second signal from the second sensor array, and transmit the sensor data to an external device.

20 Claims, 12 Drawing Sheets

(56) References Cited

U.S. PATENT DOCUMENTS

| | | | |
|---|---|---|---|
| 8,298,148 B2* | 10/2012 | Furman | A61B 5/0031 600/374 |
| 2002/0103433 A1* | 8/2002 | Muramatsu | A61B 5/02007 600/437 |
| 2005/0096557 A1* | 5/2005 | Vosburgh | A61B 5/02125 600/509 |
| 2006/0015058 A1* | 1/2006 | Kellogg | A61B 5/14514 604/22 |
| 2006/0100530 A1* | 5/2006 | Kliot | A61B 5/0002 600/483 |
| 2006/0106311 A1* | 5/2006 | Lo | A61B 5/411 600/459 |
| 2007/0244398 A1* | 10/2007 | Lo | A61B 5/02444 600/500 |
| 2011/0209373 A1 | 9/2011 | Padgett et al. | |
| 2014/0142403 A1* | 5/2014 | Brumback | A61B 5/02433 600/324 |
| 2014/0143064 A1* | 5/2014 | Tran | A61B 5/0022 705/14.66 |
| 2016/0022210 A1* | 1/2016 | Nuovo | A61B 5/681 600/301 |
| 2016/0089042 A1* | 3/2016 | Saponas | A61B 5/02438 600/437 |
| 2016/0206277 A1 | 7/2016 | Bidichandani et al. | |
| 2017/0157430 A1* | 6/2017 | Cheatham, III | A61N 7/00 |
| 2017/0209053 A1* | 7/2017 | Pantelopoulos | A61B 5/02125 |
| 2017/0231598 A1* | 8/2017 | Baek | A61B 5/0004 600/454 |
| 2017/0238817 A1* | 8/2017 | Lading | A61B 5/026 |
| 2017/0251936 A1* | 9/2017 | Sawado | A61B 8/4227 |
| 2019/0046158 A1* | 2/2019 | Kroon | A61B 8/08 |

\* cited by examiner

WEARABLE VITAL SIGN MONITOR

CROSS-REFERENCE TO RELATED APPLICATIONS

Not applicable.

BACKGROUND OF THE INVENTION

After patients are released from a hospital, they may still require health monitoring. In cases where this monitoring is not done, complications may arise and patients may return to the emergency room when the issue has escalated to a noticeable point. In many cases these complications are preventable and the escalation can be avoided if the patient's health is monitored regularly during the first several months after release. Currently, this monitoring is accomplished by the health care provider sending personnel to the home of the patient or by requiring the patient to make frequent visits to a healthcare provider. Although the current system is effective in preventing some complications, this system is limited by the frequency at which the health care provider can monitor the patient. Often, personnel limitations prevent the health care provider from checking on a patient more than a few times a week. Complications may arise between visits that could be avoided with more frequent health monitoring.

In addition to improving the patient's quality of service, this approach is also more practical in terms of reducing overall medical costs. In some cases, if a patient is readmitted to the hospital within 30 days of discharge, the hospital is liable for any additional costs incurred because it failed to provide adequate service. Hence, doing no monitoring of discharged patients can incur large costs for the health care provider. As a result, health care providers make an effort to amend this by performing periodic assessments of the discharged patients' health by sending a healthcare professional to the patient's home.

Accordingly, there is a need in the art for a remote monitoring system that would reduce the load and cost for the health care provider as it would only need to perform spot checks and visits when the remote monitoring system alerted them of a need.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a wearable vital sign monitor. The wearable vital sign monitor includes a band, where the band secures the wearable vital sign monitor relative to a user. The band includes an interior surface, the interior surface being the surface closest to the skin of the user and an exterior surface, the exterior surface opposite the interior surface. The wearable vital sign monitor also includes a first sensor array. The first sensor array is attached to the band and includes at least two sensors. The wearable vital sign monitor further includes a second sensor array. The second sensor array is attached to the band a fixed distance from the first sensor array and includes at least two sensors. The wearable vital sign monitor additionally includes an electronics module. The electronics module is configured to receive a first signal from the first sensor array, receive a second signal from the second sensor array, and transmit the sensor data to an external device.

Another example embodiment includes a remote vital sign monitoring system. The remote vital sign monitoring system includes a wearable vital sign monitor. The wearable vital sign monitor includes a band, where the band secures the wearable vital sign monitor relative to a user. The band includes an interior surface, the interior surface being the surface closest to the skin of the user and an exterior surface, the exterior surface opposite the interior surface. The wearable vital sign monitor also includes a first sensor array. The first sensor array is attached to the band and includes at least two ultrasound sensors. The wearable vital sign monitor further includes a second sensor array. The second sensor array is attached to the band a fixed distance from the first sensor array and includes at least two ultrasound sensors. The wearable vital sign monitor additionally includes a first gel pad. The first gel pad is placed on the interior surface of the band between the first sensor array and the skin of the user. The wearable vital sign monitor moreover includes a second gel pad. The second gel pad is placed on the interior surface of the band between the first sensor array and the skin of the user. The wearable vital sign monitor also includes an electronics module. The electronics module includes a battery, a logic device, a communications module, a memory, a 9-axis sensor, a temperature sensor and a sensor input. The sensor input is configured to receive a first signal from the first sensor array and receive a second signal from the second sensor array. The remote vital sign monitoring system also includes a base station. The base station is configured to send data to the communication module of the electronics module, receive sensor data from the communication module of the electronics module, and calculate one or more vital signs of the user based on the received sensor data.

Another example embodiment includes a remote vital sign monitoring system. The remote vital sign monitoring system includes a wearable vital sign monitor. The wearable vital sign monitor includes a band, where the band secures the wearable vital sign monitor on the upper arm of a user. The band includes an interior surface, the interior surface being the surface closest to the skin of the user and an exterior surface, the exterior surface opposite the interior surface. The wearable vital sign monitor also includes a first sensor array. The first sensor array is movable relative to the band, is placed above the brachial artery of the user, is attached to the band, and includes at least two piezo-electric ultrasound transceivers. The wearable vital sign monitor further includes a second sensor array. The second sensor array is movable relative to the band, is attached to the band a fixed distance from the first sensor array, is placed above the brachial artery of the user, includes at least two piezo-electric ultrasound transceivers. The wearable vital sign monitor additionally includes a first gel pad. The first gel pad is placed on the interior surface of the band between the first sensor array and the skin of the user. The wearable vital sign monitor moreover includes a second gel pad. The second gel pad is placed on the interior surface of the band between the first sensor array and the skin of the user. The wearable vital sign monitor also includes an electronics module. The electronics module includes a battery, a logic device, a communications module, a memory, a first 9-axis sensor, a temperature sensor and a sensor input. The sensor input is configured to receive a first signal from the first sensor array and receive a second signal from the second sensor array. The remote vital sign monitoring system also includes a second 9-axis sensor. The second 9-axis sensor secured to the trunk of the user near the level of the user's heart. The remote vital sign monitoring system further includes a base station. The base station is configured to send data to the communication module of the electronics module, receive sensor data from the communication module of the electronics module, receive position data from the second 9-axis sensor, and calculate from the received sensor data and the position data at least blood pressure of the user and heart rate of the user.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1:
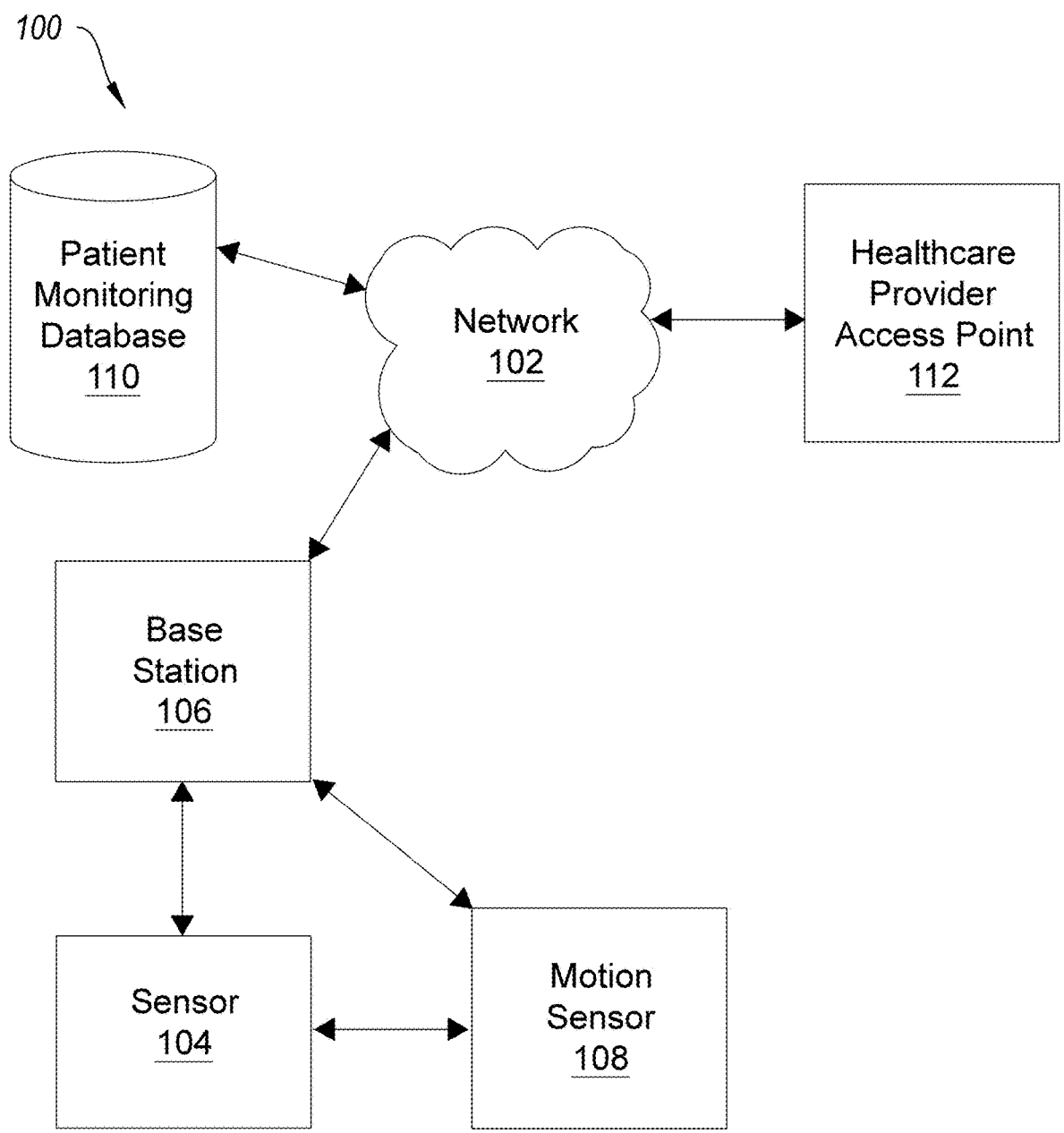
FIG. 1 illustrates a block diagram of a remote vital sign monitoring system.

FIG. 1 illustrates a block diagram of a remote vital sign monitoring system 100. The remote vital sign monitoring system 100 allows for remote monitoring of a patient's vital signs by a health care provider. For example, the patient may be at home or another remote location, or at a hospital or other care facility. If a vital sign goes outside of acceptable levels the remote vital sign monitoring system 100 alerts the health care provider and/or other designated entities who may then take further action as necessary.

FIG. 1 shows that the remote vital sign monitoring system 100 can include a network 102. In at least one implementation, the network 102 can be used to connect the various parts of the system 100 to one another. The network 102 exemplarily includes the Internet, including a global internetwork formed by logical and physical connections between multiple wide area networks and/or local area networks and can optionally include the World Wide Web ("Web"), including a system of interlinked hypertext documents accessed via the Internet. Alternately or additionally, the network 102 includes one or more cellular RF networks and/or one or more wired and/or wireless networks such as, but not limited to, 802.xx networks, Bluetooth access points, wireless access points, IP-based networks, or the like. For example, the network 102 can include cloud based networking and computing. The network 102 can also include servers that enable one type of network to interface with another type of network.

FIG. 1 also shows that the remote vital sign monitoring system 100 can include a sensor 104. The sensor 104 is configured to monitor one or more vital signs of a patient. For example, the sensor 104 can measure blood pressure, pulse rate, axillary temperature, motion, respiration rate or other vital signs. The sensor 104 is placed on the body of the user. Making the sensor and any connected hardware as small as possible allows a user to retain as much freedom of motion and independence as possible.

As used in the specification and the claims, the phrase "configured to" denotes an actual state of configuration that fundamentally ties recited elements to the physical characteristics of the recited structure. That is, the phrase "configured to" denotes that the element is structurally capable of performing the cited element but need not necessarily be doing so at any given time. Thus, the phrase "configured to" reaches well beyond merely describing functional language or intended use since the phrase actively recites an actual state of configuration.

FIG. 1 further shows that the remote vital sign monitoring system 100 can include a base station 106. The base station 106 communicates with the sensor 104 and transmits the desired data over network 102. That is, the base station 106 acts as a bridge between sensor 104 and network 102. The base station 106 can include any device capable of receiving communication from the sensor 104 and transmitting over the network 102. For example, the base station 102 can include a network connected device such as a smart device.

The base station 106 acts as a relay station for the sensor data between the sensor and the authorized health care provider. In addition, the base station 106 offloads processing, storage, and communication tasks from the sensor 104 in order to conserve battery power in the sensor 104. Although the primary purpose of the base station 106 is as an information relay between the sensor and the health care provider, the base station 106 can also act as a display and visualization mechanism for the user to access their past data and/or to ensure that the sensor 104 is functioning properly. The base station 106 should maintain a high level of security and/or encryption with the data as it transfers over the network 102 to ensure the patient's privacy.

The base station 106 can include devices such as a smartphone, a computer, a tablet, a Bluetooth enabled cellphone, a Bluetooth enabled tablet, a laptop or desktop computer with Bluetooth connectivity, or a Qualcomm 2net connectivity device, etc. that has the ability to communicate with the sensor 104 through Bluetooth or another secure wireless connection and connect to the network 102 through a wired, wireless, and/or cellular connection using standard, secure internet protocols. Bluetooth is an open wireless technology standard for exchanging data over short distances (using short-wavelength radio transmissions in the ISM band from 2400-2480 MHz) from fixed and mobile devices, creating personal area networks (PANs) with high levels of security. For example, the communication can be accomplished using a Bluetooth low energy (BLE) module or some other device.

FIG. 1 also shows that the remote vital sign monitoring system 100 can include a motion sensor 108. The motion sensor 108 is located on the trunk of the user. For example, the motion sensor 108 can be located level with the heart of the user. The motion sensor 108 can include a 9-axis sensor. If the sensor 104 likewise includes a 9-axis sensor then the distance between, and relative motion of, the sensor 104 and the motion sensor 108 can be calculated at any given time by the base station 106. One of skill in the art will appreciate that the sensor 104 and the motion sensor 108 may communicate with one another directly or communicate through the base station 106 as needed.

FIG. 1 additionally shows that the remote vital sign monitoring system 100 can include a patient monitoring database 110. The patient monitoring database 110 stores vital sign information for each patient, allowing historical data to be stored and for alerts to be created when needed. For example, if the patient's blood pressure exceeds a certain threshold then the patient monitoring database 110 can send an alert to a health care provider or desired contact.

FIG. 1 moreover shows that the remote vital sign monitoring system 100 can include a health care provider access point 112. The health care provider access point 112 allows a health care provider to view or otherwise access patient data. For example, the health care provider access point 112 can allow a nurse or doctor to view the patient's data over a specified period of time and/or review an alert regarding the patient.

Figure 2A:
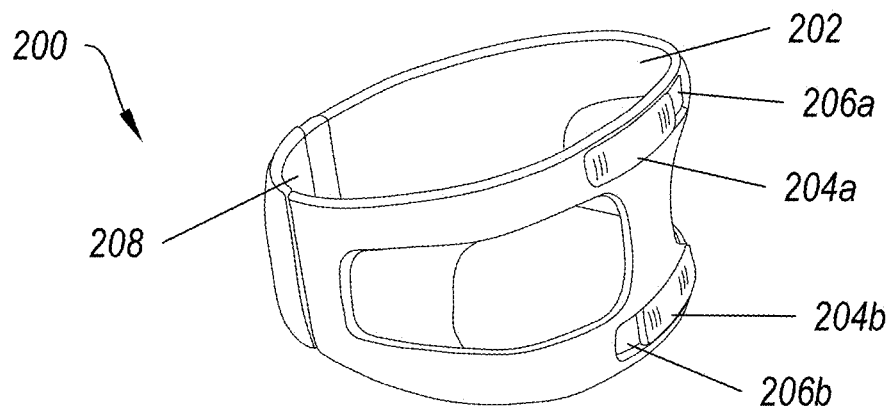
FIG. 2A illustrates a perspective view of the example of a wearable vital sign monitor.
Figure 2B:
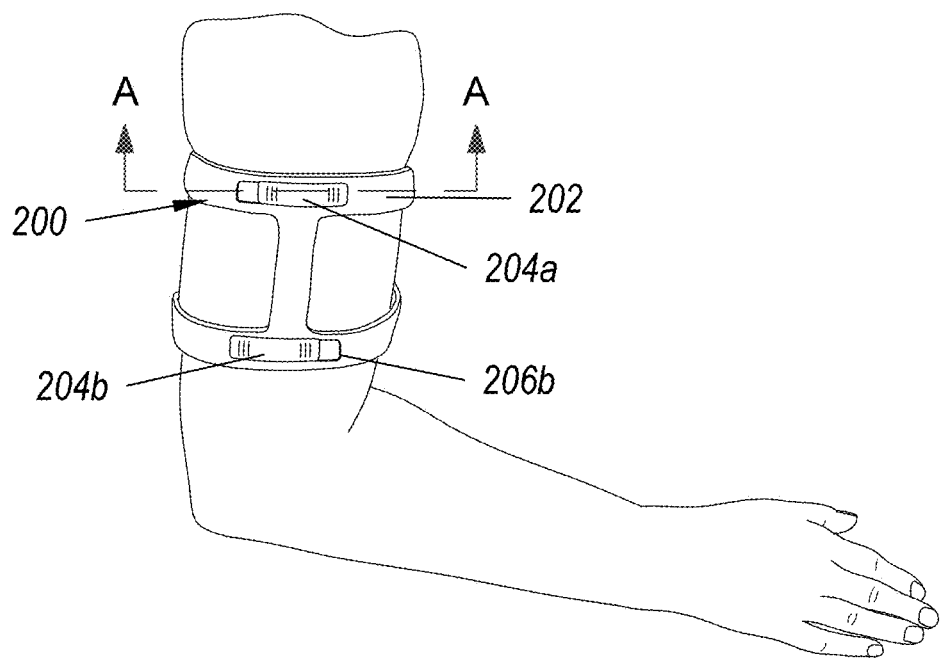
FIG. 2B illustrates an example of the wearable vital sign monitor on the arm of a user.
Figure 2C:
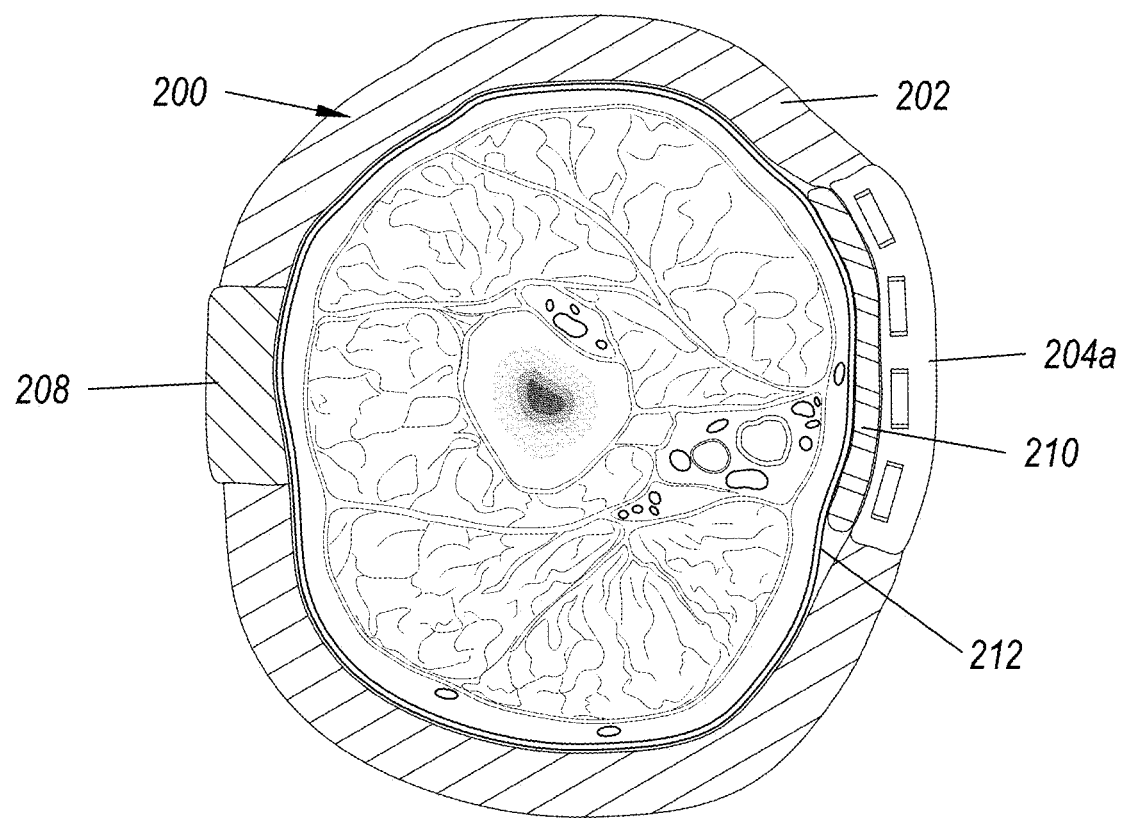
FIG. 2C illustrates a cross section of FIG. 2B along the line A-A.

FIGS. 2A, 2B and 2C (collectively "FIG. 2") illustrate an example of a wearable vital sign monitor 200. FIG. 2A illustrates a perspective view of the example of a wearable vital sign monitor 200; FIG. 2B illustrates an example of the wearable vital sign monitor 200 on the arm of a user; and FIG. 2C illustrates a cross section of FIG. 2B along the line A-A. The wearable vital sign monitor 200 can be used as the sensor 104 of the remote vital sign monitoring system 100 of FIG. 1. The wearable vital sign monitor 200 can measure blood pressure, pulse rate, axillary temperature, motion, respiration rate or other vital signs. In addition, the wearable vital sign monitor 200 can detect some abnormal vital signs (arrhythmias), and arterial health or wellness.

The wearable vital sign monitor 200 can be placed on the brachial artery (inside of the upper arm) on the patient. One of skill in the art will appreciate that other arterial locations be used but that the brachial artery is a convenient spot for many patients as it allows freedom of movement and allows access to the hand and wrist for other medical devices and tasks as necessary. The wearable vital sign monitor 200 measures pulse transit time (PTT) using continuous wave Doppler at two locations on the upper arm but pulsed wave Doppler or even phased array pulsed or continuous Doppler could also be used.

FIG. 2 shows that the wearable vital sign monitor 200 can include a band 202. The band 202 positions the other portions of the wearable vital sign monitor 200 relative to one another and allows the wearable vital sign monitor 200 to be secured relative to the user. For example, the band 202 can allow the wearable vital sign monitor 200 to be placed on the upper arm of the user where it will remain in place. The band 202 can be made of any suitable material. For example, the band 202 can include molded plastic, cloth, rubber, or any other desired material and can be secured with buckles, hook and loop fasteners, etc.

FIG. 2 also shows that the wearable vital sign monitor 200 can include a first sensor array 204a and a second sensor array 204b (collectively "sensor arrays 204"). The sensor arrays 204 will be on the same band, a fixed distance apart (e.g., the first sensor array 204a can be approximately three inches from the second sensor array 204b). The sensor arrays 204 include multiple piezo-electric transducers. Because the brachial artery isn't straight using sensor arrays 204 allows for a single wearable vital sign monitor 200 to automatically adjust to obtain the strongest signal on an individual patient, as described below. For example, the sensor arrays 204 can each include four sensors, with the sensor receiving the strongest signal during any measurement period selected automatically. As used in the specification and the claims, the term approximately shall mean that the value is within 10% of the stated value, unless otherwise specified.

The sensor arrays 204 are movable relative to the band 202 for calibration purposes. For example, FIG. 2 further shows that the first sensor array 204a and the second sensor array 204b are in first slot 206a and second slot 206b (collectively "slots 206"). The slots 206 allow the sensor arrays 204 to be positioned during calibration, as described below. I.e., the slots allow the sensor arrays to be moved to find the best position on the wearable vital sign monitor 200 relative to the brachial artery. When the desired position is achieved the position of the sensor arrays 204 relative to the slots 206 can be locked or otherwise fixed.

Further, the band 202 ensures that the sensor arrays 204 remain a fixed distance apart. The fixed distance allows for ease in vital sign calculations. I.e., the fixed distance removes a variable from vital sign calculations, making calibration easier and providing more accurate calculations of vital signs. For example, blood pressure can be calculated using pulse transit time and pulse wave velocity, as described below.

FIG. 2 additionally shows that the wearable vital sign monitor 200 can include an electronics module 208. The electronics module 208 can include electronics that allow for vital sign measuring and protect electronics from coming into contact with the patient. For example, the electronics module can include a communications module, a power source, a processor, or any other desired electronic components, as described below.

FIG. 2 moreover shows that the wearable vital sign monitor 200 can include a gel pad 210. The gel pad 210 is inserted between the sensor arrays 204 and the skin 212 of the user. The gel pad couples the ultrasound energy to the tissue, providing an impedance match between the transducer and the tissue. For example, ultrasound waves do not propagate well in air, which can cause most of the energy to be reflected back into the transducer transmitter. This makes it almost impossible to get a return signal with the shift. With the gel pad 210 the ultrasound penetrates the tissue and the moving blood cells create a doppler shift in the return signal, and the impedance mismatch. Therefore, the presence of gel pad 210 can be critical to getting the doppler signal. The use of a fluid gel is well known in the art as a coupling agent for ultrasound imaging. These gels however contain water that can quickly evaporate, the use of a gel pad accomplishes the impedance matching with an element that is more stable over time, and less prone to evaporation.

The gel pad 210 can include any desired gel that allows the effective transmission of the ultrasound waves into the tissue. For example, the gel can include propylene glycol, glycerine, perfume, dyes, phenoxyethanol or carbapol R 940 polymer, agar-gar, gelatin and water. The gel pad 210 can include a plastic shell or covering that retains the gel and allows for easy placement by the user.

Figure 3:
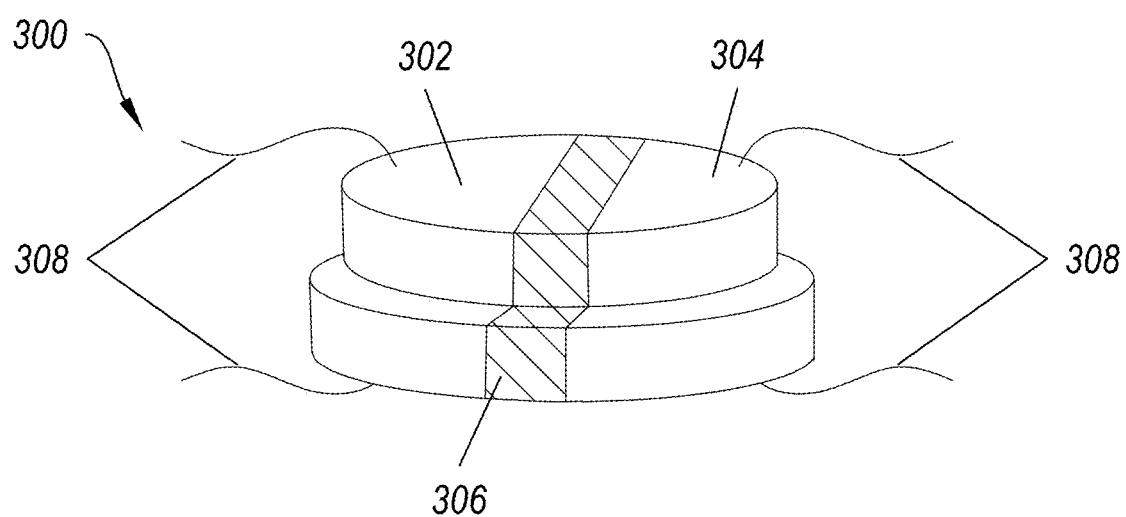
FIG. 3 illustrates an example of an ultrasound transceiver.

FIG. 3 illustrates an example of an ultrasound transceiver 300. The ultrasound transceiver 300 detects a pulse wave in the artery of a user. For example, the ultrasound transceiver 300 can be used in the sensor arrays 204 of FIG. 2. An ultrasound transceiver 300 includes a number of benefits relative to photo sensors or other sensors. For example, the ultrasound transceiver 300 sees only arterial velocity (reduces or eliminates noise) which gives more accurate readings and can measure pulse wave velocity directly (not deriving it from other collected data) using the Doppler effect. Further, the ultrasound transceiver 300 does not get interference from the user's other tissues (such as muscle) and the fixed distance between sensor arrays can be smaller than with other sensor types. Moreover, the ultrasound transceiver 300 is more comfortable and easy to wear for the individual user and allows measurements to all occur on the upper arm of the user, which means the wearable vital sign monitor does not get in the way of other things nurses might have to do at the wrist or elbow region of the user.

FIG. 3 shows that the ultrasound transceiver 300 can include a transmitter 302. The beam pattern of the transmitter 302 can be determined by the active transmitter area and shape, the ultrasound wavelength, and the sound velocity of the propagation medium. The transmitter 302 converts an electrical signal into sound waves. For example, the transmitter 302 can include a piezoelectric crystal. Piezoelectric crystals change size and shape when a voltage is applied; AC voltage makes them oscillate at the same frequency and produce ultrasonic waves.

Ultrasound transmitters can also use non-piezoelectric principles. such as magnetostriction. Materials with this property change size slightly when exposed to a magnetic field. The diaphragm (or membrane) principle is also used in micro-machined ultrasonic transducers (MUTs). These devices are fabricated using silicon micro-machining technology (MEMS technology), which is particularly useful for the fabrication of transducer arrays. The vibration of the diaphragm may be measured or induced electronically using the capacitance between the diaphragm and a closely spaced backing plate (CMUT), or by adding a thin layer of piezoelectric material on diaphragm (PMUT).

One of skill in the art will appreciate that the ultrasound frequency produced by the transmitter 302 can be critical to ensure accuracy and patient safety. For example, frequencies that are two low may penetrate deeply and cover a wide area, getting unwanted signals and frequencies that are too high don't penetrate deeply and cover a narrow area. Further, the penetration of the ultrasound waves needs to be sufficient to detect the doppler shift of the blood in the patient's artery but should be restricted to just enough to produce an accurate signal. Thus, the ideal penetration depth is between 1.5-2 inches but may vary for different patients. Therefore, the frequency may be between 3 MHz and 7 MHz. More specifically, the frequency may be between 3 MHz and 4 MHz.

FIG. 3 also shows that the ultrasound transceiver 300 can include a receiver 304. The receiver 304 receives the reflected ultrasound waves and converts them to electric signals. Since piezoelectric materials generate a voltage when force is applied to them, they can also work as ultrasonic detectors. Some systems use separate transmitters and receivers, while others combine both functions into a single piezoelectric transceiver. A capacitor ("condenser") microphone has a thin diaphragm that responds to ultrasound waves. Changes in the electric field between the diaphragm and a closely spaced backing plate convert sound signals to electric currents, which can be amplified.

FIG. 3 further shows that the ultrasound transceiver 300 can include an isolation region 306. The isolation region 306 ensures that the transmitter 302 and the receiver 304 remain physically, acoustically and electronically separate from one another. That is, the isolation region 306 prevents physical contact, electric signals and ultrasound waves from the transmitter 302 propagating directly to the receiver 304. For example, the isolation region 306 can be an empty space or a cut through a whole disk that separates the transmitter 302 and the receiver 304.

FIG. 3 additionally shows that the ultrasound transceiver 300 can include one or more electrical connections 308. The electrical connections 308 allow a voltage to be applied to the transmitter 302, for the creation of ultrasonic waves, and/or allow a voltage to be produced at the receiver 304, when ultrasonic waves are detected. Thus, the electrical connections 308 provide power to the transmitter 302 and allow the receiver 304 to transmit an electrical signal.

Figure 4:
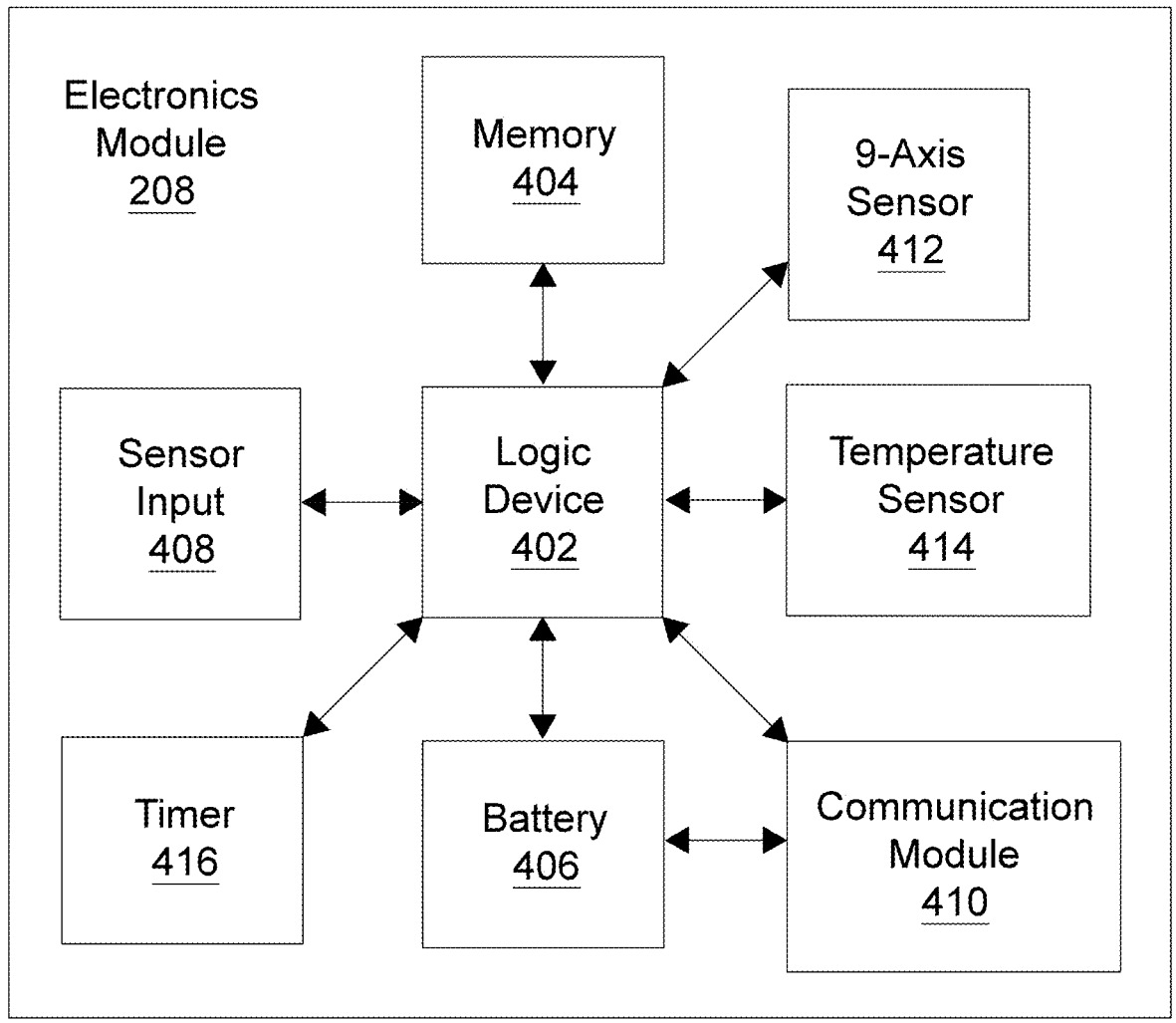
FIG. 4 illustrates a block diagram of an electronics module.

FIG. 4 illustrates a block diagram of an electronics module 208. The electronics module 208 controls the operation of a wearable vital sign monitor. For example, the electronics module can coordinate operation of the sensors and reception of sensor data.

FIG. 4 shows that the electronics module 208 can include a logic device 402. A logic device 402 can include any device capable of performing logic functions. For example, the logic device 402 can perform Boolean logic or can produce a predetermined output based on input. The logic device 402 can include ROM memory, programmable logic device (PLD), programmable array logic (PAL), generic array logic (GAL), complex programmable logic device (CPLD), field programmable gate arrays (FPGA), logic gates, processors or any other device capable of performing logic functions.

The logic device 402 can control the functions of the other components of the electronics module 208. In particular, the logic device 402 can ensure that the components of the electronics module 208 perform their desired function at the appropriate time and in the appropriate manner. The timing of functions can be critical to ensure that vital signs are correctly calculated and that appropriate information is transmitted to a health care provider.

For example, the logic device 402 can include a microcontroller. A microcontroller (sometimes abbreviated μC, μC or MCU) is a small computer on a single integrated circuit containing a processor core, memory, and programmable input/output peripherals. Program memory in the form of NOR flash or one time programmable ROM is also often included on chip, as well as a typically small amount of RAM. Microcontrollers will generally have the ability to retain functionality while waiting for an event such as a button press or other interruption; power consumption while sleeping (CPU clock and most peripherals off) may be just nanowatts, making many of them well suited for long lasting battery applications.

FIG. 4 further shows that the electronics module 208 can include a memory 404. The memory 404 can include any device capable of storing data in computer readable form. The memory 404 can include volatile memory and non-volatile memory. Volatile memory can include dynamic random access memory (DRAM), static random access memory (SRAM), thyristor random access memory (T-RAM), zero capacitor random access memory (Z-RAM), twin transistor random access memory (TTRAM), delay line memory, selectron tube and williams tube. Non-volatile memory can include read-only memory (ROM), programmable read only memory (PROM), erasable programmable read only memory (EPROM), electrically erasable programmable read only memory (EEPROM), flash memory, ferroelectric random access memory (FeRAM), magnetoresistive random access memory (MRAM), phase change random access memory (PRAM, aka PCM, PRAM, PCRAM, ovonic unified Memory, chalcogenide random access memory and C-RAM), conductive-bridging random access memory (CBRAM aka. programmable metallization cell or PMC), silicon-oxide-nitride-oxide-silicon (SONOS), resistive random-access memory (RRAM), racetrack memory, nano random access memory (NRAM), millipede, drum memory, magnetic core memory, plated wire memory, bubble memory and twistor memory.

FIG. 4 additionally shows that the electronics module 208 can include a battery 406 or other power source. A battery 406 is a device that includes one or more electrochemical cells that convert stored chemical energy into electrical energy. For example, the battery 406 can include a rechargeable battery and a power input (for charging the battery 406). A rechargeable battery includes one or more electrochemical cells and its electrochemical reactions are electrically reversible. Rechargeable batteries come in many different shapes and sizes, ranging from button cells to megawatt systems connected to stabilize an electrical distribution network. Several different combinations of chemicals are commonly used, including: lead-acid, nickel cadmium (NiCd), nickel metal hydride (NiMH), lithium ion (Li-ion), and lithium ion polymer (Li-ion polymer).

FIG. 4 moreover shows that the electronics module 208 can include a sensor input 408. The sensor input 408 receives information from one or more external sensors. In particular, the sensor input 408 is an electrical input that allows for electrical signals from a sensor to be processed by the logic device 402. One of skill in the art will appreciate that multiple sensor inputs 408 may be present to allow for multiple sensor signals to be received and processed.

FIG. 4 also shows that the electronics module 208 can include a communication module 410. For example, the communication module 410 can include a Bluetooth low energy ("BLE") module. Bluetooth is an open wireless technology standard for exchanging data over short distances (using short-wavelength radio transmissions in the ISM band from 2400-2480 MHz) from fixed and mobile devices, creating personal area networks (PANs) with high levels of security. I.e., the communication module 410 allows data to be sent from the electronics module 208 to an external device, such as a base station, and vice versa.

FIG. 4 further shows that the electronics module 208 can include a 9-axis sensor 412. The 9-axis sensor 412 includes a motion sensor that can detect movements with high accuracy. The 9-axis sensor includes a 3-axis gyroscope, a 3-axis accelerometer, and a 3-axis magnetometer (sometimes referred to as a 3-axis compass). The gyroscope and accelerometer provide information about accelerations in all three directions, and rotations around each axis. Gravity provides a background direction from the accelerometer, so we can do a pretty good job of tracking short term movements. However, in order to track the real position and orientation in space, the 6-axis sensor is not sufficient because small errors build up in each axis and over time these errors can add up to a drift in the absolute direction. This problem is overcome by adding one more absolute directional sensor—a 3-axis magnetometer. The extra magnetic field information allows the sensing algorithms to compensate for small drifts over much longer periods of time, so the absolute change in position and orientation can be tracked much more accurately. Therefore, the 9-axis sensor 412 allows for measure and tracking of location and orientation precisely during very complex movements.

FIG. 4 additionally shows that the electronics module 208 can include a temperature sensor 414. The temperature sensor 414 allows the temperature of the user to be monitored. In particular, the skin temperature near the band can be monitored. In addition, the temperature sensor 414 can allow the temperature of the electronics module to be monitored. For example, the temperature sensor 414 can ensure that the electronics module 208 does not overheat and injure the user.

FIG. 4 moreover shows that the electronics module 208 can include a timer 416. The timer 416 ensures that the testing for vital signs occurs when desired. For example, the timer 416 can be used by the logic device to determine when the vital sign of the user should be measured, as described below. One of skill in the art will appreciate that the time 416 may be an independent module or can be combined with another module, such as the logic device 402.

Figure 5:
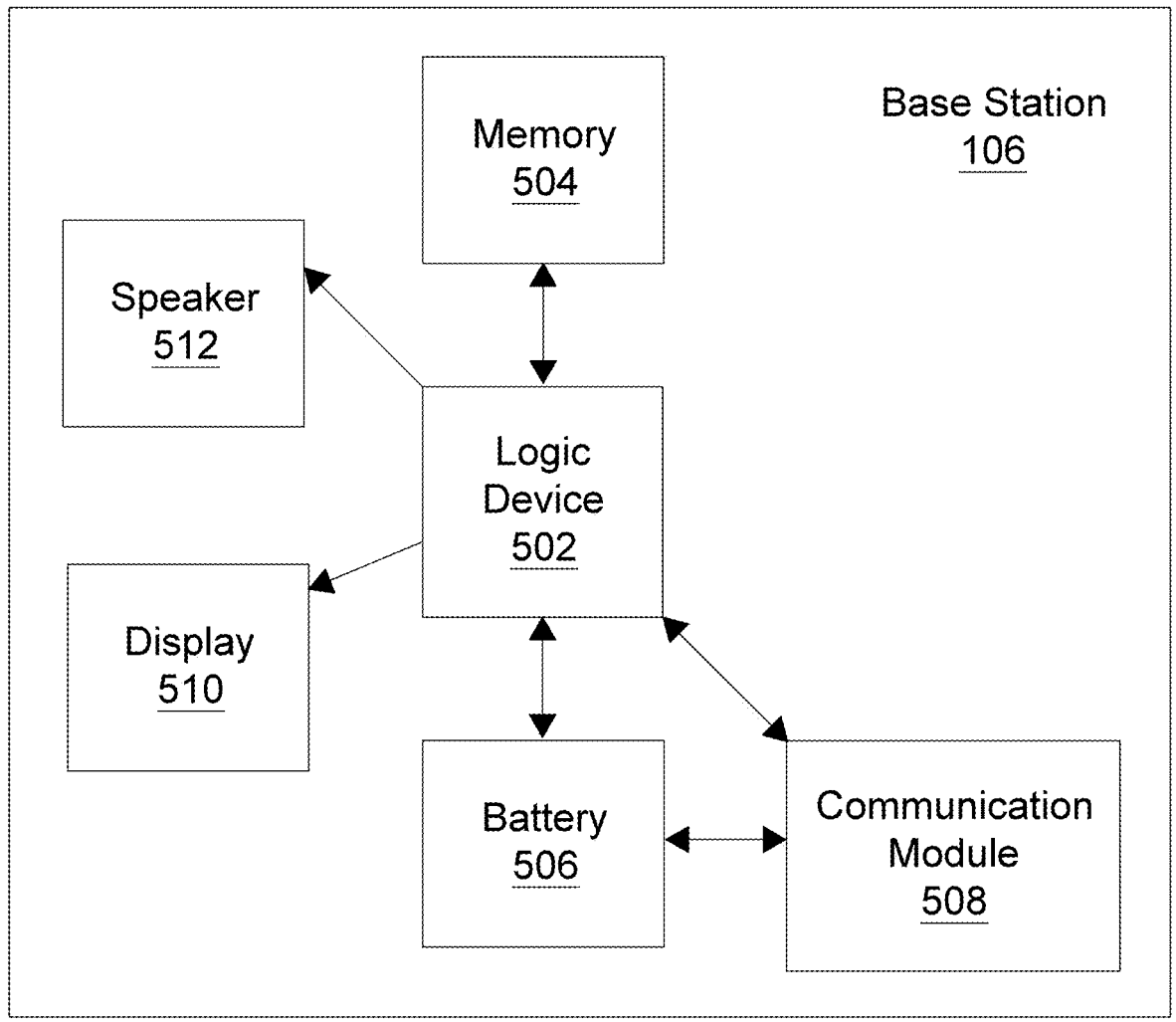
FIG. 5 illustrates a block diagram of an example of a base station.

FIG. 5 illustrates a block diagram of an example of a base station 106. The base station 106 can offload much of the processing and computing requirements of a wearable vital sign monitor. That is, the wearable vital sign monitor can just obtain data which is sent to the base station 106, thus reducing the power and size requirements of the wearable vital sign monitor and any potential heating problems of the wearable vital sign monitor.

FIG. 5 shows that the base station 106 can include a logic device 502. A logic device 502 can include any device capable of performing logic functions. For example, the logic device 502 can perform Boolean logic or can produce a predetermined output based on input. The logic device 502 can include ROM memory, programmable logic device (PLD), programmable array logic (PAL), generic array logic (GAL), complex programmable logic device (CPLD), field programmable gate arrays (FPGA), logic gates, processors or any other device capable of performing logic functions.

The logic device 502 can control the functions of the other components of the base station 106. In particular, the logic device 502 can ensure that the components of the base station 106 perform their desired function at the appropriate time and in the appropriate manner. The timing of functions can be critical to ensure that vital signs are correctly calculated and that appropriate information is transmitted to a health care provider.

For example, the logic device 502 can include a microcontroller. A microcontroller (sometimes abbreviated µC, µC or MCU) is a small computer on a single integrated circuit containing a processor core, memory, and programmable input/output peripherals. Program memory in the form of NOR flash or one time programmable ROM is also often included on chip, as well as a typically small amount of RAM. Microcontrollers will generally have the ability to retain functionality while waiting for an event such as a button press or other interruption; power consumption while sleeping (CPU clock and most peripherals off) may be just nanowatts, making many of them well suited for long lasting battery applications.

FIG. 5 further shows that the base station 106 can include a memory 504. The memory 504 can include any device capable of storing data in computer readable form. The memory 504 can include volatile memory and non-volatile memory. Volatile memory can include dynamic random access memory (DRAM), static random access memory (SRAM), thyristor random access memory (T-RAM), zero capacitor random access memory (Z-RAM), twin transistor random access memory (TTRAM), delay line memory, selectron tube and williams tube. Non-volatile memory can include read-only memory (ROM), programmable read only memory (PROM), erasable programmable read only memory (EPROM), electrically erasable programmable read only memory (EEPROM), flash memory, ferroelectric random access memory (FeRAM), magnetoresistive random access memory (MRAM), phase change random access memory (PRAM, aka PCM, PRAM, PCRAM, ovonic unified memory, chalcogenide random access memory and C-RAM), conductive-bridging random access memory (CBRAM aka. programmable metallization cell or PMC), silicon-oxide-nitride-oxide-silicon (SONOS), resistive random-access memory (RRAM), racetrack memory, nano random access memory (NRAM), millipede, drum memory, magnetic core memory, plated wire memory, bubble memory and twistor memory.

FIG. 5 additionally shows that the base station 106 can include a battery 506 or other power source. A battery 506 is a device that includes one or more electrochemical cells that convert stored chemical energy into electrical energy. For example, the battery 506 can include a rechargeable battery and a power input (for charging the battery 506). A rechargeable battery includes one or more electrochemical cells and its electrochemical reactions are electrically reversible. Rechargeable batteries come in many different shapes and sizes, ranging from button cells to megawatt systems connected to stabilize an electrical distribution network. Several different combinations of chemicals are commonly used, including: lead-acid, nickel cadmium (NiCd), nickel metal hydride (NiMH), lithium ion (Li-ion), and lithium ion polymer (Li-ion polymer).

FIG. 5 also shows that the base station 106 can include a communication module 508. For example, the communication module 508 can include a Bluetooth low energy ("BLE") module. Bluetooth is an open wireless technology standard for exchanging data over short distances (using short-wavelength radio transmissions in the ISM band from 2400-2480 MHz) from fixed and mobile devices, creating personal area networks (PANs) with high levels of security. I.e., the communication module 508 allows data to be sent from the base station 106 to a wearable vital sign monitor and vice versa.

In addition, the communication module 508 can send data over a network, such as the network 102 of FIG. 1, to be accessed by a healthcare provider. That is, the communication module 508 can establish a secure connection where data is sent as needed to personnel who can then monitor or review the vital signs of the user. For example, the communication module 508 can communicate via an Ethernet connection, Wi-Fi, or any other desired communications protocol.

FIG. 5 further shows that the base station 106 can include a display 510. The display 510 can be used to show desired data to a user. For example, if a wearable vital sign monitor is being used to measure the blood pressure of a user, then the display 510 can show the most recent blood pressure measurement and/or a history of blood pressure measurements. Additionally, the display 510 can include lights or other status indicators. For example, the display 510 can include lights to indicate signal strength, battery level, connection to sensors, transmission of data to a health care provider, etc.

FIG. 5 moreover shows that the base station 106 can include a speaker 512. The speaker 512 can produce audio signals to communicate data to a user. For example, the speaker 512 can be used to produce audio messages for a user. In addition, the speaker 512 can provide audio signals during calibration of a wearable vital sign monitor, allowing for acquisition of the best possible signal, as described below.

Figure 6:
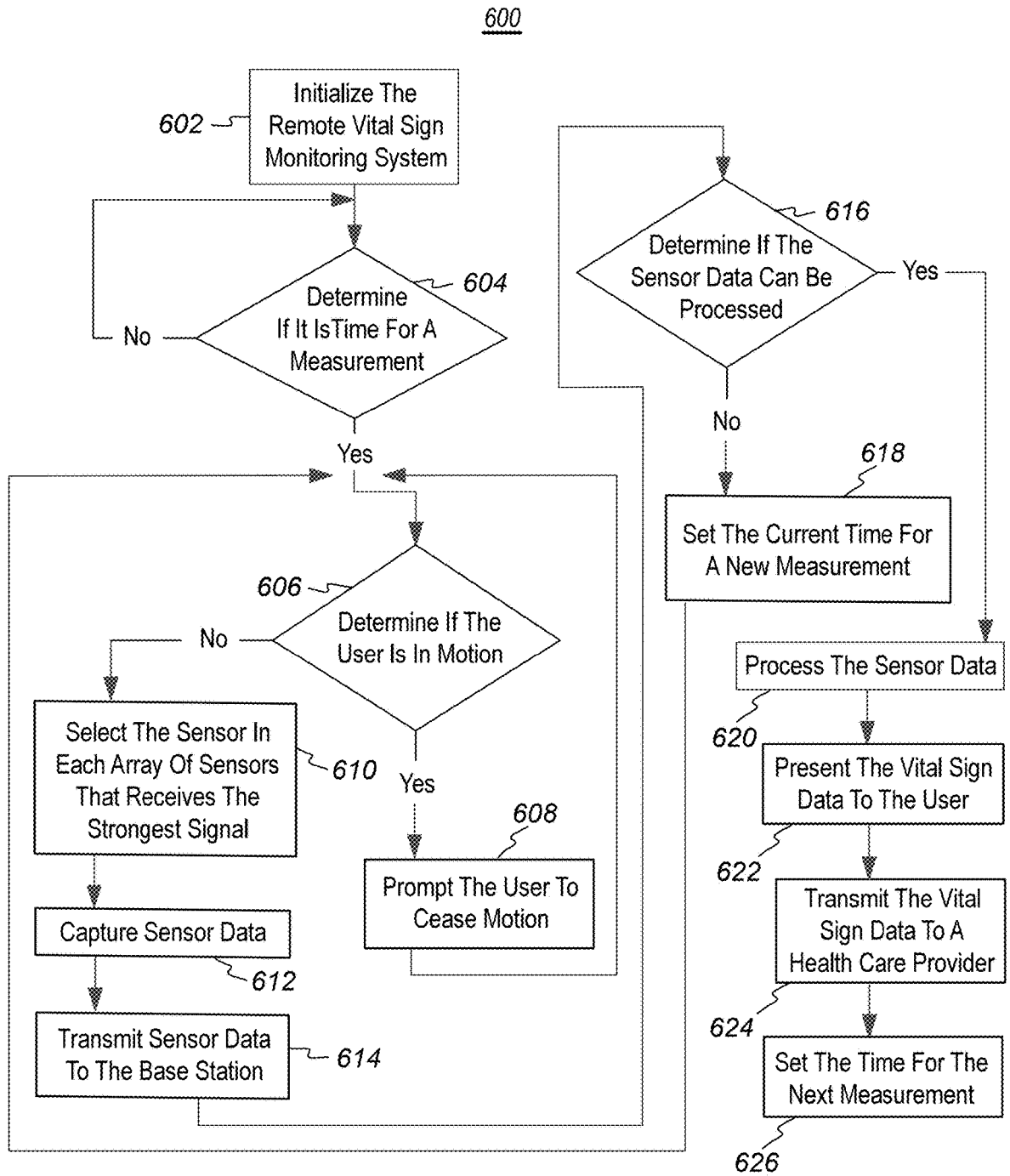
FIG. 6 is a flowchart illustrating a method for monitoring a user's vital sign.

FIG. 6 is a flowchart illustrating a method 600 for monitoring a user's vital sign. In at least one implementation, the user's vital signs can be measured using a remote vital sign monitoring system, such as the remote vital sign monitoring system 100 of FIG. 1. Therefore, the method 600 will be described, exemplarily, with reference to the remote vital sign monitoring system 100 of FIG. 1. Nevertheless, one of skill in the art can appreciate that the method 600 can be used with a remote vital sign monitoring system other than the remote vital sign monitoring system 100 of FIG. 1.

FIG. 6 shows that the method 600 can include initializing 602 the remote vital sign monitoring system. For example, the remote vital sign monitoring system can be initialized using the method 700 of FIG. 7. Initializing 602 allows the remote vital sign monitoring system to begin monitoring of an individual patient. For example, initialization 602 includes startup and calibration of the system to the individual user.

FIG. 6 also shows that the method 600 can include determining 604 if it is time for a measurement. Most vital signs do not require continuous measurement. For example, blood pressure can be measured for 30 seconds every 30 minutes. Thus, any inconvenience experienced by the user is minimized. In addition, ultrasound sensors do not provide a tactile or audio sensation, like blood pressure cuffs and other devices, therefore measurements can be done nonintrusively. A timer or other time keeping mechanism can be used to determine 604 if it is time for a measurement.

FIG. 6 further shows that the method 600 can include determining 606 if the user is in motion when it is time for a measurement. Motion by the user can cause incorrect readings. For example, if the user is walking and swinging his/her arms then measurements may not be accurate.

FIG. 6 additionally shows that the method 600 can include prompting 608 the user to cease motion if the user is in motion. For example, the base station may include an audio or visual message that indicates to the user that he/she cease motion. One of skill in the art will appreciate that the user may not be prompted 608 unless the motion continues for a period of time. For example, if motion is detected then another check may be done after a preset period of time (e.g., 15 seconds) and if three checks in a row all detect motion then the prompt may be given.

FIG. 6 moreover shows that the method 600 can include selecting 610 the sensor in each array of sensors that receives the strongest signal. That is, each sensor in an array of sensors can make measurements and the sensor with the strongest signal is selected as the sensor to be used in that array of sensors. Thus, the user need not move or adjust the wearable vital sign monitor to obtain accurate readings.

FIG. 6 also shows that the method 600 can include capturing 612 sensor data. E.g., PWV and temperature readings can be made to determine vital signs of the user. The sensor data can be a digital signal or an analog signal that is translated to a digital signal.

FIG. 6 further shows that the method 600 can include transmitting 614 sensor data to the base station. I.e., the communications module is used to send the sensor data. Because the raw data is sent, the transmission distance is short and calculations can be delegated to the base station the power requirements for the wearable vital sign monitor can be reduced, as described above.

FIG. 6 also shows that the method 600 can include determining 616 if the sensor data can be processed. That is, it is determined 616 if the sensor data is usable for calculating the vital sign. For example, if data is missing or corrupted then the sensor data cannot be processed.

FIG. 6 moreover shows that the method 600 can include setting 618 the current time for time for a new measurement if the sensor data cannot be processed. That is, the method is returned to step 606 to perform new measurements to obtain usable data. One of skill in the art will appreciate that if a number of attempts have failed then the system may be shut down and/or the user may be asked to perform certain actions with the system (restart, recalibrate, etc.).

FIG. 6 additionally shows that the method 600 can include processing 620 the sensor data if the sensor data can be processed. In addition, the sensor data can be processed 620 to ensure that the data is usable. That is, the sensor data is checked to ensure that it is within the range of expected values and that each data point that is necessary for calculations is present. In addition, the data can be processed 620 by calculating the desired vital signs. For example, the PWV can be used to calculate blood pressure of the user.

FIG. 6 also shows that the method 600 can include presenting 622 the vital sign data to the user. For example, the measured vital sign can be visually presented to the user on a display at the base station or the measured vital sign can be spoken to the user via the speaker of the base station. The vital sign data can also be presented 622 as a trend. For example, the vital sign data can be shown as the last five measurements of the vital sign.

FIG. 6 further shows that the method 600 can include transmitting 624 the vital sign data to a health care provider. The data can be transmitted 624 after each cycle or can be transmitted at predetermined points (e.g., once a day). Additionally or alternatively, the data can be transmitted 624 at the request of the user and/or health care provider. I.e., when a healthcare provider logs onto a health care provider access point and selects the user, the base station can receive a message to transmit 624 the vital sign data.

FIG. 6 additionally shows that the method 600 can include setting 626 the time for the next measurement. For example, a timer can be started, at the end of which the method 600 will return to step 606. The timer may be based on the vital sign being measured and/or the user. For example, high risk user's may have vital signs measured more frequently.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 7:
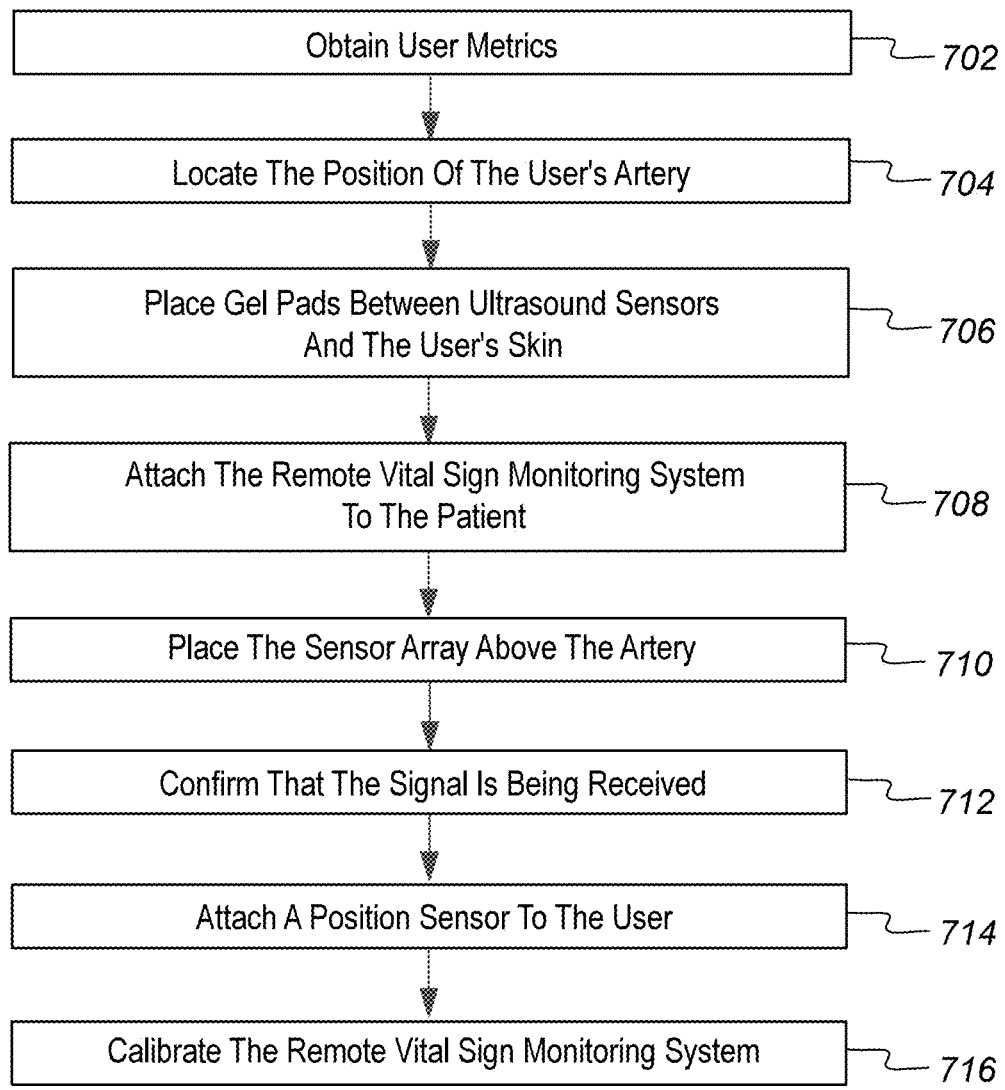
FIG. 7 is a flowchart illustrating a method for initializing a remote vital sign monitoring system.

FIG. 7 is a flowchart illustrating a method 700 for initializing a remote vital sign monitoring system. In at least one implementation, the user's vital signs can be measured using a remote vital sign monitoring system, such as the remote vital sign monitoring system 100 of FIG. 1. Therefore, the method 700 will be described, exemplarily, with reference to the remote vital sign monitoring system 100 of FIG. 1. Nevertheless, one of skill in the art can appreciate that the method 700 can be used with a remote vital sign monitoring system other than the remote vital sign monitoring system 100 of FIG. 1.

FIG. 7 shows that the method 700 can include obtaining 702 user metrics. User metrics include any physiological data that is relevant for monitoring the user's vital signs. For example, user metrics can include the user's upper arm length. The user metrics can be obtained 702 by entering the data manually, with the use of a nomogram to estimate upper arm length using well know parameters such as height and weight, or by an actual measurement.

FIG. 7 also shows that the method 700 can include locating 704 the position of the user's artery. For example, a health care provider can palpate the position of the user's artery. Palpating the position of the user's artery includes examining the user via touch to locate 704 the position of the artery. For example, the position of the user's brachial artery in the upper arm can be located 704. The position of the user's artery may be noted as a line rather than a point. For example, the position of the user's brachial artery may be located 704 along a length of the user's inner upper arm. Once the artery position has been located 704, the position may be marked for future reference.

FIG. 7 further shows that the method 700 can include placing 706 gel pads between ultrasound sensors and the user's skin. The gel pads are placed on the interior of any ultrasound sensors. The gel pads will typically last for several days and easily replaced by the user. As described above, the gel pads provide acoustic coupling to the tissue. The gel pads may have an attachment mechanism, such as adhesive, that allows the gel pad to remain in position once placed 706.

FIG. 7 additionally shows that the method 700 can include attaching 708 the remote vital sign monitoring system to the patient. For example, the center of the remote vital sign monitoring system (i.e., the midpoint between the sensor arrays) can be placed approximately level with the patient's heart with the user's arm at his/her side. The remote vital sign monitoring system can be attached 708 to the patient by securing the band with hook and loop fasteners or any other desired fastener.

FIG. 7 moreover shows that the method 700 can include placing 710 the sensor array above the artery. For example, the middle of the sensor array can be placed directly over the artery located 704 previously. The sensor array will automatically select the sensor that receives the best signal, therefore, the sensor array need not be placed exactly over the artery.

FIG. 7 also shows that the method 700 can include confirming 712 that the signal is being received. That is, after the sensor array is placed 710 above the user's artery the sensory should begin to detect the pulse wave through the user's artery. The signal can be confirmed 712 using base station (e.g., a smart device app). For example, the speaker on the base station can produce an audio signal that allows verification that the Doppler signal is being received by both arrays.

FIG. 7 further shows that the method 700 can include attaching 714 a position sensor to the user. The position sensor allows for calibration of the remote vital sign monitoring system and allows for correction of vital sign readings based on the relative position of the vital sign monitoring system to the level of the center of the heart. (i.e., the position of the artery relative to the user's heart), as described below. For example, the position sensor can include a 9-axis sensor attached 714 to the mid axillary position on the side of the user's chest at heart level. This can be computed by using the difference of the angles of the two 9-axis sensors (one in the monitor on the arm and the other on the chest wall) and knowing that the arm is attached to the trunk (torso) at the shoulder. This trunk located motion sensor should also be able to reinforce the determination of the respiration rate.

FIG. 7 additionally shows that the method 700 can include calibrating 716 the remote vital sign monitoring system. Calibrating 716 the remote vital sign monitoring system ensures that the data produced by the remote vital sign monitoring system are accurate. That is, calibrating 716 the remote vital sign monitoring system ensures that the system will accurately measure the user's vital signs.

Figure 8:
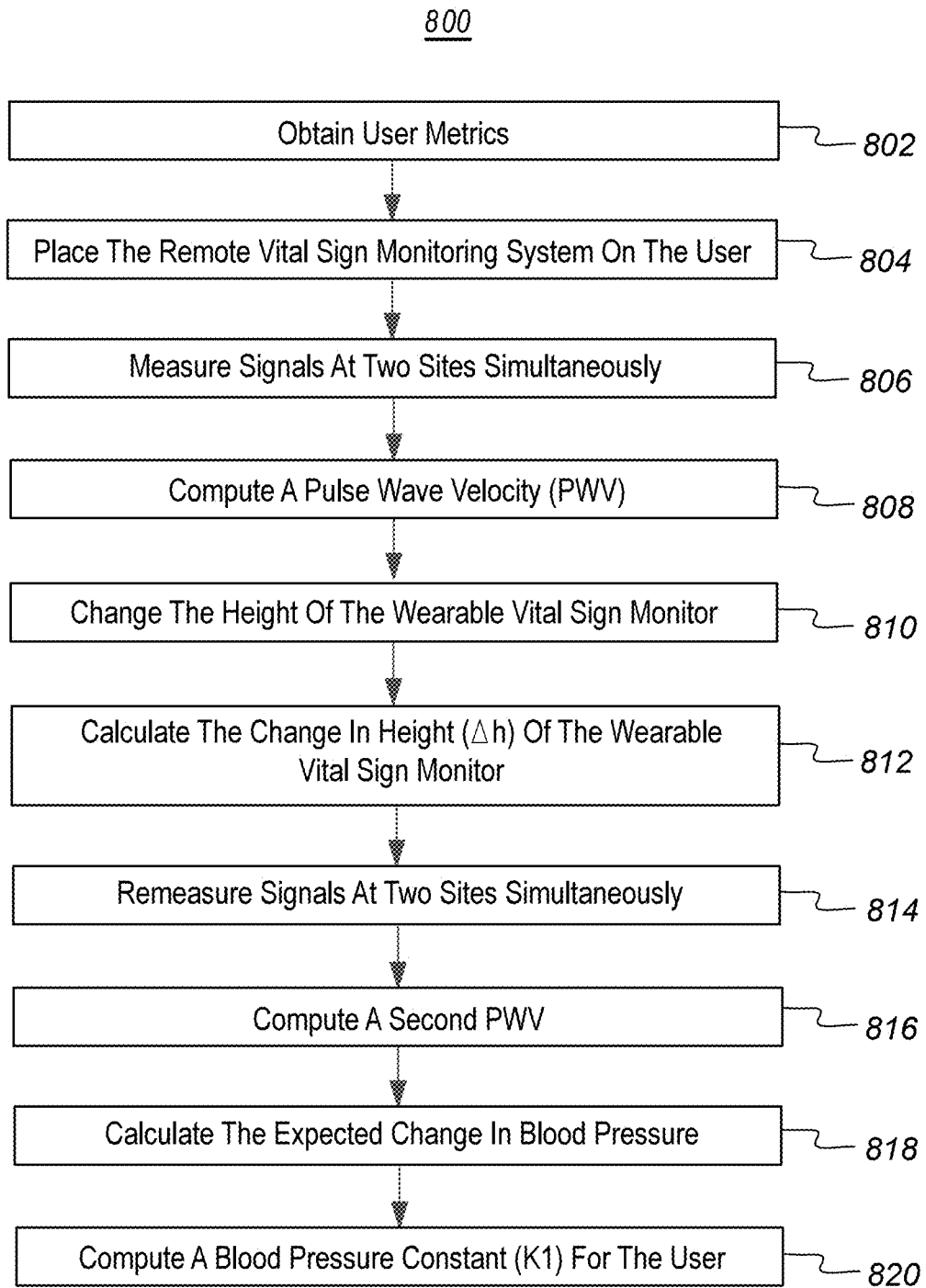
FIG. 8 is a flowchart illustrating a method for calibrating a remote vital sign monitoring system.

FIG. 8 is a flowchart illustrating a method 800 for calibrating a remote vital sign monitoring system. In at least one implementation, the user's vital signs can be measured using a remote vital sign monitoring system, such as the remote vital sign monitoring system 100 of FIG. 1. Therefore, the method 800 will be described, exemplarily, with reference to the remote vital sign monitoring system 100 of FIG. 1. Nevertheless, one of skill in the art can appreciate that the method 800 can be used with a remote vital sign monitoring system other than the remote vital sign monitoring system 100 of FIG. 1.

FIG. 8 shows that the method 800 can include obtaining 802 user metrics. User metrics include any physiological data that is relevant for monitoring the user's vital signs. For example, user metrics can include the user's upper arm length. The user metrics can be obtained 802 by entering the data manually or by measuring. For example, the user's upper arm length can be measured using one or more 9-axis sensors.

FIG. 8 also shows that the method 800 can include placing 804 the remote vital sign monitoring system on the user. For example, a wearable vital sign monitor can be placed on the user's upper arm and a 9-axis sensor can be placed on the user's trunk at heart level.

FIG. 8 further shows that the method 800 can include measuring 806 signals at two sites simultaneously. For example, the two sites can be measured using a pair of sensor arrays. The signals at the two sites are measured to determine the time difference between the same event (e.g., diastole and systole portions of the cardiac cycle).

FIG. 8 additionally shows that the method 800 can include computing 808 a pulse wave velocity (PWV). PWV, by definition, is the distance traveled by the wave divided by the time for the wave to travel that distance using the formula:

$$PWV = \frac{\Delta x}{\Delta t} \qquad \text{Equation 1}$$

Because the distance is known between the measurement points, the time difference is measured and the PWV is a straightforward calculation. This holds true for a system with zero wave reflections. The transmission of the arterial pressure pulse does not give the true PWV as it is a sum of vectors of the incident and reflected waves so the event is chosen to occur without wave reflections.

FIG. 8 additionally shows that the method 800 can include changing 810 the height of the wearable vital sign monitor. For example, if the wearable vital sign monitor is on the arm of the user, the user can raise his/her arm above his/her head. This naturally results in a lower blood pressure in the brachial artery of the user.

FIG. 8 moreover shows that the method 800 can include calculating 812 the change in height ($\Delta h$) of the wearable vital sign monitor. E.g., the 9-axis sensor in the wearable vital sign monitor and the 9-axis sensor on the user's trunk are each reporting position. At the initial measurement point, they will be some distance apart in height. Once the user raises his/her arm the height difference between the two 9-axis sensors will change. The change in the height difference is $\Delta h$.

FIG. 8 also shows that the method 800 can include remeasuring 814 signals at two sites simultaneously. For example, the two sites can be measured using a pair of sensor arrays. The signals at the two sites are measured to determine the time difference between the same event (e.g., diastole and systole portions of the cardiac cycle).

FIG. 8 further shows that the method 800 can include computing 816 a second PWV (i.e., by using Equation 1). Because the distance has not changed between the measurement points, the time difference is measured and the PWV remains a straightforward calculation.

FIG. 8 additionally shows that the method 800 can include calculating 818 the expected change in blood pressure. I.e., the change in height of the artery results in an expected change in blood pressure. Typically, a $\Delta h$ of +10 cm above the heart level is expected to result in a decrease in blood pressure of 7.4 mmHg (millimeters of mercury) although there are a number of factors, such as blood density, that can affect the expected change. The expected change in blood pressure is directly proportional to the expected change in PWV using the relationship above.

FIG. 8 moreover shows that the method 800 can include computing 820 a blood pressure constant (K1) for the user. Blood pressure is directly proportional to PWV. However, the exact relationship can vary from user to user. Thus, K1 accounts for these variations and allows for an accurate measurement of an individual user's blood pressure. Because variables, such as arterial stiffness, change slowly over time, K1 allows for calculations of blood pressure based on the PWV of the user.

By way of example, assume the first PWV ($PWV_1$) is computed 808 as 3.5 m/s and the second PWV ($PWV_2$) is computed 816 as 2.5 m/s and the $\Delta h$ between $PWV_1$ and $PWV_2$ is determined 812 to be 35 cm. The expected change in blood pressure is 25.2 mmHg. If the calculated difference is 16.8 mmHg, then K1 is computed 820 as 1.5 for that user. Thus, all PWV calculations are multiplied by 1.5 to give the true PWV for that user. Blood pressure is then a straightforward calculation for that user (typically done by using a lookup table or fitting to an exponential curve).

Figure 9:
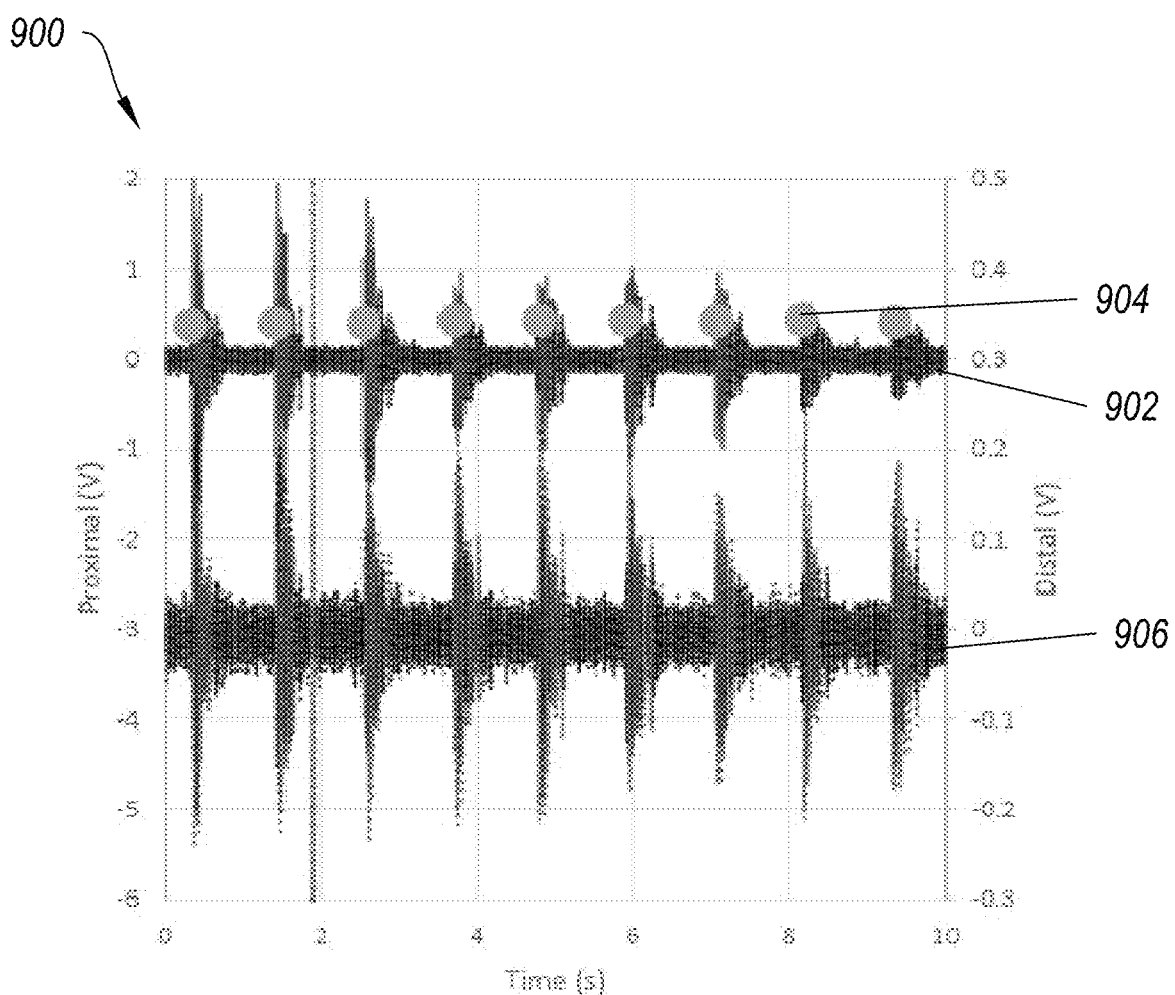
FIG. 9 illustrates an example of ultrasound data obtained for a user.

FIG. 9 illustrates an example of ultrasound data 900 obtained for a user. The ultrasound data is obtained by two sensors a fixed distance from one another. Thus, a measurement of the PTT can allow calculations of the PWV.

FIG. 9 shows that the ultrasound data includes a proximal sensor waveform 902. The proximal sensor waveform 902 is the data from the sensor closest to the heart (higher on the arm if using the brachial artery). Because the Doppler signal occurs at the same rate as the heartbeat, a pulse rate can be calculated based on the timing of the beats. For example, Table 1 shows the measured pulse locations 904 on the proximal waveform 902 and the calculated pulse rate.

TABLE 1

| Pulse | Proximal time (s) | Diff | Pulse Rate |
|---|---|---|---|
| 1 | 0.3437 | | |
| 2 | 1.4309 | 1.0872 | 55.18763797 |
| 3 | 2.564 | 1.1331 | 52.95207837 |
| 4 | 3.7219 | 1.1579 | 51.81794628 |
| 5 | 4.799 | 1.0771 | 55.70513416 |
| 6 | 5.9164 | 1.1174 | 53.69608019 |
| 7 | 7.0498 | 1.1334 | 52.93806247 |
| 8 | 8.1592 | 1.1094 | 54.08328826 |
| 9 | 9.3085 | 1.1493 | 52.20569042 |
| | | AVG | 53.57323976 |
| | | Measured | 54 |

FIG. 9 also shows that the ultrasound data includes a distal sensor waveform 906. The distal sensor waveform 906 is the data from the sensor farthest from the heart (lower on the arm if using the brachial artery). The difference in time between the proximal sensor waveform 902 and the distal sensor waveform 906 for an individual event is the PTT.

Figure 10:
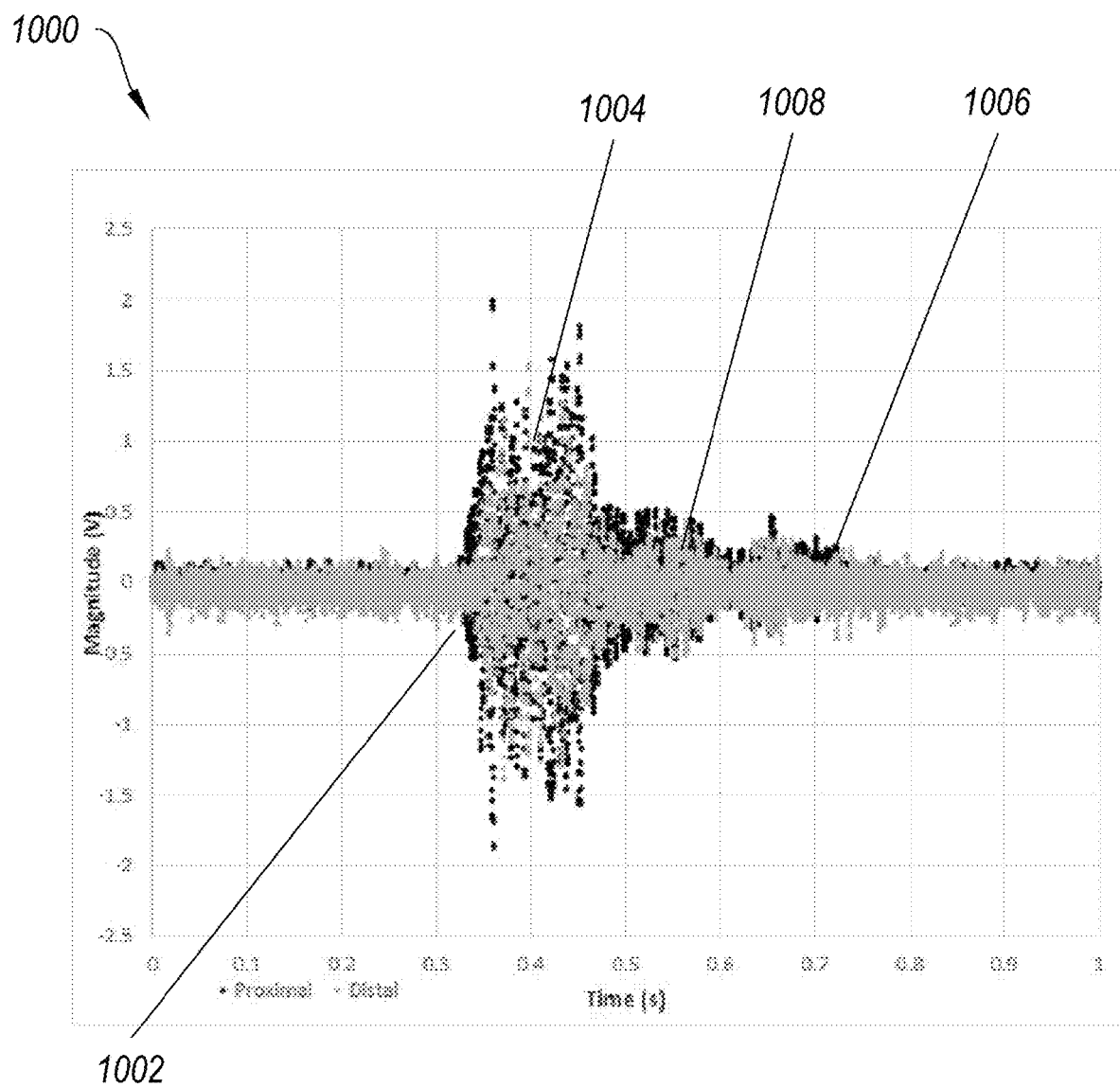
FIG. 10 illustrates an example of a set of waveforms for a single heartbeat.

FIG. 10 illustrates an example of a set of waveforms 1000 for a single heartbeat. Within the set of waveforms 1000:

Beginning of Systole (BS) 1002 is the beginning of the doppler waveform as the blood begins to move forward in the artery. It represents the biggest change in velocity in the blood.

Peak Systolic Velocity (PSV) 1004 is the maximum velocity of the blood. It corresponds to systole and the highest pressure in the arterial blood.

End Systolic Velocity (ESV) 1006 is the lowest sustained velocity of the blood. It corresponds to diastole and the lowest pressure in the arterial blood.

There is a very short period during the beginning of diastole when the blood flows backwards in the vessel as the aortic valve closes and the forward momentum stops. This is labeled as early diastolic reversal 1008.

The timing of these events past the two sensors and the distance between the sensors can be used to calculate the Pulse Wave Velocity (PWV) in the artery. Further information derived either by an external calibration data or by hydrostatic induced offsets to the pressure, allow the device to compute the pressure in the artery at various points in the waveform. The pressure at systole, and diastole and a MAP can be computed and displayed.

Using these events, the waveforms of FIG. 9 can be analyzed to give the blood pressures of Table 2:

TABLE 2

| | Beginning of Systole (BS) | | | Peak Systolic Velocity (PSV) | | | End Systolic Velocity (ESV) | | |
|---|---|---|---|---|---|---|---|---|---|
| Pulse | Prox | Dist | Diff | Prox | Dist | Diff | Prox | Dist | Diff |
| 1 | 0.3309 | 0.3473 | 0.0164 | 0.4004 | 0.4091 | 0.0087 | 0.7373 | 0.7539 | 0.0166 |
| 2 | 1.4107 | 1.4277 | 0.017 | 1.4608 | 1.4696 | 0.0088 | 1.7644 | 1.7809 | 0.0165 |
| 3 | 2.5349 | 2.552 | 0.0171 | 2.6192 | 2.6281 | 0.0089 | 2.8992 | 2.916 | 0.0168 |
| 4 | 3.6983 | 3.7162 | 0.0179 | 3.7706 | 3.779 | 0.0084 | 4.0585 | 4.0763 | 0.0178 |
| 5 | 4.7728 | 4.7911 | 0.0183 | 4.7967 | 4.805 | 0.0083 | 5.1336 | 5.1517 | 0.0181 |
| 6 | 5.8975 | 5.9153 | 0.0178 | 5.9802 | 5.9888 | 0.0086 | 6.2864 | 6.3042 | 0.0178 |
| 7 | 7.0501 | 7.0671 | 0.017 | 7.1194 | 7.1281 | 0.0087 | 7.4581 | 7.4753 | 0.0172 |
| 8 | 8.1405 | 8.1579 | 0.0174 | 8.1703 | 8.1788 | 0.0085 | 8.5119 | 8.5293 | 0.0174 |
| 9 | 9.3081 | 9.3255 | 0.0174 | 9.3727 | 9.3812 | 0.0085 | 9.7096 | 9.7275 | 0.0179 |
| | | AVG | 0.017366667 | | AVG | 0.0085875 | | AVG | 0.0174375 |
| | | Measured pressure (mmHg) | 94 | | Measured pressure (mmHg) | 147 | | Measured pressure (mmHg) | 94 |

Thus, the user's blood pressure is 147/94.

Figure 11:
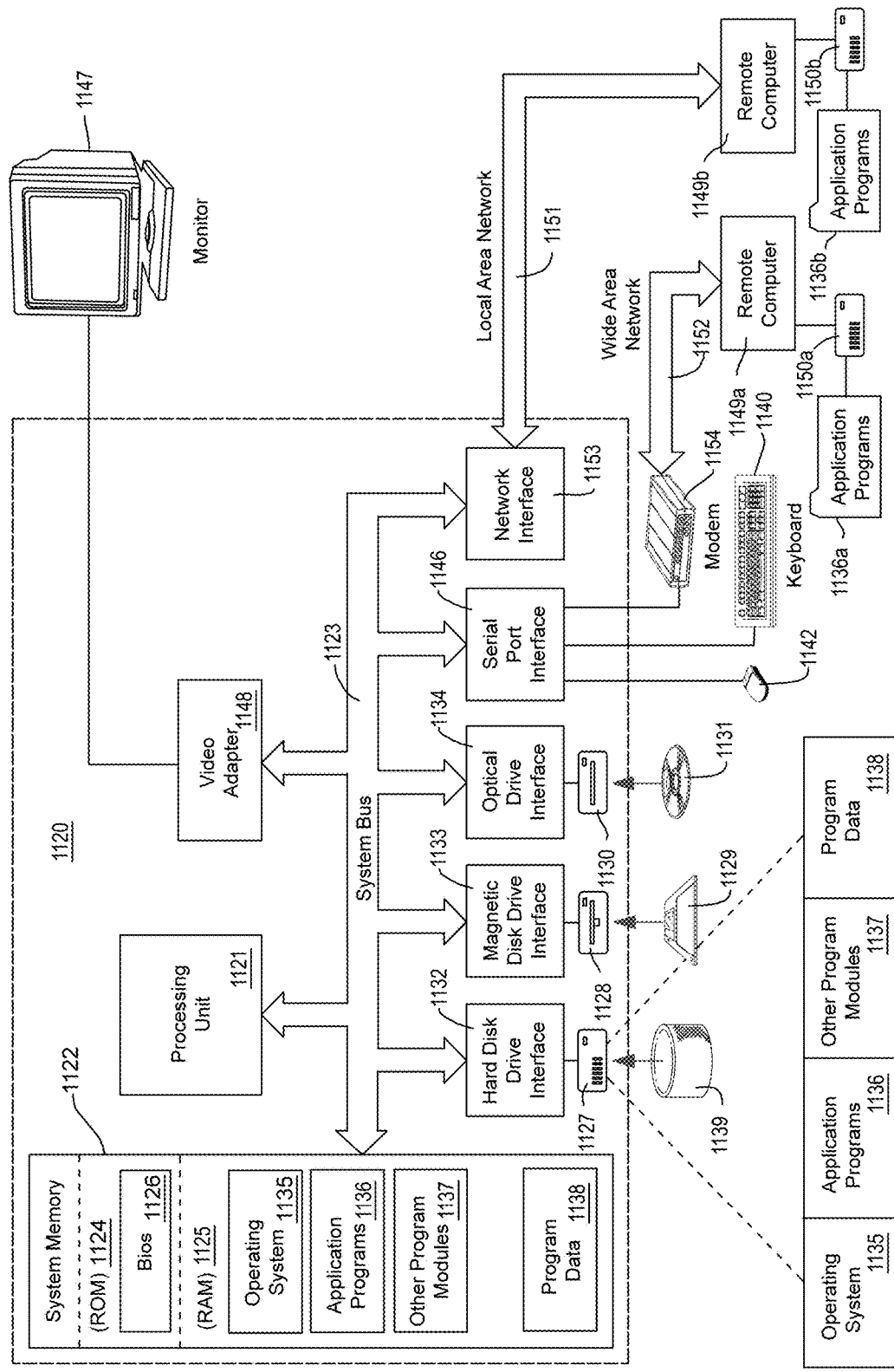
FIG. 11 illustrates an example of a suitable computing environment in which the invention may be implemented.

FIG. 11, and the following discussion, are intended to provide a brief, general description of a suitable computing environment in which the invention may be implemented. Although not required, the invention will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

One of skill in the art will appreciate that the invention may be practiced in network computing environments with many types of computer system configurations, including personal computers, hand-held devices, mobile phones, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 11, an example system for implementing the invention includes a general purpose computing device in the form of a conventional computer 1120, including a processing unit 1121, a system memory 1122, and a system bus 1123 that couples various system components including the system memory 1122 to the processing unit 1121. It should be noted however, that as mobile phones become more sophisticated, mobile phones are beginning to incorporate many of the components illustrated for conventional computer 1120. Accordingly, with relatively minor adjustments, mostly with respect to input/output devices, the description of conventional computer 1120 applies equally to mobile phones. The system bus 1123 may be any of several types of bus structures including a memory bus or memory controller, a peripheral bus, and a local bus using any of a variety of bus architectures. The system memory includes read only memory (ROM) 1124 and random access memory (RAM) 1125. A basic input/output system (BIOS) 1126, containing the basic routines that help transfer information between elements within the computer 1120, such as during start-up, may be stored in ROM 1124.

The computer 1120 may also include a magnetic hard disk drive 1127 for reading from and writing to a magnetic hard disk 1139, a magnetic disk drive 1128 for reading from or writing to a removable magnetic disk 1129, and an optical disc drive 1130 for reading from or writing to removable optical disc 1131 such as a CD-ROM or other optical media. The magnetic hard disk drive 1127, magnetic disk drive 1128, and optical disc drive 1130 are connected to the system bus 1123 by a hard disk drive interface 1132, a magnetic disk drive-interface 1133, and an optical drive interface 1134, respectively. The drives and their associated computer-readable media provide nonvolatile storage of computer-executable instructions, data structures, program modules and other data for the computer 1120. Although the exemplary environment described herein employs a magnetic hard disk 1139, a removable magnetic disk 1129 and a removable optical disc 1131, other types of computer readable media for storing data can be used, including magnetic cassettes, flash memory cards, digital versatile discs, Bernoulli cartridges, RAMs, ROMs, and the like.

Program code means comprising one or more program modules may be stored on the hard disk 1139, magnetic disk 1129, optical disc 1131, ROM 1124 or RAM 1125, including an operating system 1135, one or more application programs 1136, other program modules 1137, and program data 1138. A user may enter commands and information into the computer 1120 through keyboard 1140, pointing device 1142, or other input devices (not shown), such as a microphone, joy stick, game pad, satellite dish, scanner, motion detectors or the like. These and other input devices are often connected to the processing unit 1121 through a serial port interface 1146 coupled to system bus 1123. Alternatively, the input devices may be connected by other interfaces, such as a parallel port, a game port or a universal serial bus (USB). A monitor 1147 or another display device is also connected to system bus 1123 via an interface, such as video adapter 1148. In addition to the monitor, personal computers typically include other peripheral output devices (not shown), such as speakers and printers.

The computer 1120 may operate in a networked environment using logical connections to one or more remote computers, such as remote computers 1149a and 1149b. Remote computers 1149a and 1149b may each be another personal computer, a server, a router, a network PC, a peer device or other common network node, and typically include many or all of the elements described above relative to the computer 1120, although only memory storage devices 1150a and 1150b and their associated application programs 1136a and 1136b have been illustrated in FIG. 11. The logical connections depicted in FIG. 11 include a local area network (LAN) 1151 and a wide area network (WAN) 1152 that are presented here by way of example and not limitation. Such networking environments are commonplace in office-wide or enterprise-wide computer networks, intranets and the Internet.

When used in a LAN networking environment, the computer 1120 can be connected to the local network 1151 through a network interface or adapter 1153. When used in a WAN networking environment, the computer 1120 may include a modem 1154, a wireless link, or other means for establishing communications over the wide area network 1152, such as the Internet. The modem 1154, which may be internal or external, is connected to the system bus 1123 via the serial port interface 1146. In a networked environment, program modules depicted relative to the computer 1120, or portions thereof, may be stored in the remote memory storage device. It will be appreciated that the network connections shown are exemplary and other means of establishing communications over wide area network 1152 may be used.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A wearable vital sign monitor, the wearable vital sign monitor comprising:
    a band including an interior surface and an exterior surface opposite the interior surface, the band defining a circumferential direction and a longitudinal direction perpendicular to the circumferential direction;
    a first slot extending in the circumferential direction of the band;
    a second slot spaced apart from the first slot a fixed distance in the longitudinal direction, the second slot also being aligned along the circumferential direction of the band;
    a first ultrasound sensor array attached to the band and disposed within the first slot, the first ultrasound sensor array being configured to be moveable within the first slot so as to be selectively positionable at different circumferential positions within the first slot;
    a second ultrasound sensor array attached to the band a fixed longitudinal distance from the first ultrasound sensor array in the second slot, a second ultrasound sensor array being configured to be moveable within the second slot so as to be selectively positionable at different circumferential positions within the second slot,
    wherein the band is configured to allow placement on an upper arm of a user, and wherein the first and second ultrasound arrays are selectively positionable at the different circumferential positions within the respective first and second slot to enable each to be positioned above the brachial artery of the upper arm of the user; and
    an electronics module, wherein the electronics module is configured to:
        receive a first signal from the first ultrasound sensor array;
        receive a second signal from a second ultrasound sensor array; and
        transmit sensor data received from the first and second ultrasound arrays to an external device.

2. The wearable vital sign monitor of claim 1, further comprising: a gel pad disposed on the interior surface of the band.

3. The wearable vital sign monitor of claim 1, wherein the first sensor array includes a plurality of ultrasound sensors and wherein the second sensor array includes a plurality of ultrasound sensors.

4. The wearable vital sign monitor of claim 3, wherein the fixed distance is approximately three inches.

5. The wearable vital sign monitor of claim 1, wherein the electronics module includes a 9-axis motion sensor.

6. The wearable vital sign monitor of claim 1, wherein the electronics module includes a temperature sensor.

7. A remote vital sign monitoring system, comprising:
the wearable vital sign monitor of claim 1; and
a base station configured to receive sensor data from the electronics module and calculate one or more vital signs of the user based on the received sensor data.

8. The remote vital sign monitoring system of claim 7, wherein the electronics module of the wearable vital sign monitor includes a first motion sensor, the monitoring system further comprising a separate, second motion sensor configured for attachment to the user at a location separate from the wearable vital sign monitor.

9. The remote vital sign monitoring system of claim 8, wherein the base station is configured to:
receive position data from the first and second position sensors;
determine a position of the wearable vital sign monitor relative to the second position sensor, including a distance of the wearable vital sign monitor from the second position sensor that varies according to the relative positions of the wearable vital sign monitor and the second position sensor; and
calculate one or more vital signs based on both the received sensor data and on the distance of the wearable vital sign monitor apart from the second position sensor.

10. A remote vital sign monitoring system, the remote vital sign monitoring system comprising:
a wearable vital sign monitor, the wearable vital sign monitor including:
a band including an interior surface and an exterior surface opposite the interior surface, the band defining a circumferential direction and a longitudinal direction perpendicular to the circumferential direction;
a first sensor array attached to the band within a first slot that extends in the circumferential direction of the band, the first sensor array including at least two ultrasound sensors and being moveable relative to the band through selective circumferential movement within the first slot;
a second sensor array attached to the band a fixed longitudinal distance from the first sensor array within a second slot that extends in the circumferential direction of the band, the second sensor array including at least two ultrasound sensors and being moveable relative to the band and the first sensor array through selective circumferential movement within the second slot,
wherein the band is configured to allow placement on an upper arm of a user, and wherein the first and second sensor arrays are selectively positionable at the different circumferential positions within the respective first and second slot to enable each to be positioned above the brachial artery of the upper arm of the user;
one or more gel pads positioned over the first and second sensor arrays and disposed on the interior surface of the band;
an electronics module configured to receive a first signal from the first sensor array and receive a second signal from the second sensor array; and
a base station configured to receive sensor data from the electronics module and calculate one or more vital signs of the user based on the received sensor data.

11. The remote vital sign monitoring system of claim 10, wherein the base station includes: a video display; and an audio speaker.

12. The remote vital sign monitoring system of claim 10, wherein the base station includes a smart device.

13. The remote vital sign monitoring system of claim 10, wherein the base station includes: a memory; a logic device; a battery; and a communications module.

14. The remote vital sign monitoring system of claim 10, wherein the electronics module includes a first position sensor disposed in the electronics module and a second, separate position sensor configured for attachment to a trunk of a user, wherein the base station is further configured to:
receive position data from the first and second position sensors;
determine a position of the wearable vital sign monitor relative to the second position sensor, including a distance of the wearable vital sign monitor from the second position sensor that varies according to the relative positions of the wearable vital sign monitor and the second position sensor; and
calculate one or more vital signs based on both the received sensor data and on the distance of the wearable vital sign monitor apart from the second position sensor.

15. The remote vital sign monitoring system of claim 14, wherein the one or more calculated vital signs comprises a blood pressure measurement, the calculated blood pressure measurement being based in part on the determined position of the wearable vital sign monitor relative to the second position sensor.

16. The remote vital sign monitoring system of claim 15, wherein the base station is configured to determine the position of the wearable vital sign monitor relative to the second position sensor at least in part by calculating a change in height of the wearable vital sign monitor relative to the second position sensor.

17. A remote vital sign monitoring system, the remote vital sign monitoring system comprising:
a wearable vital sign monitor, the wearable vital sign monitor including:
a band configured in size and shape to allow attachment to an upper arm of a user, the band including an interior surface and an exterior surface opposite the interior surface;
a first sensor array that is attached to the band, movable relative to and within the band in a circumferential direction of the band, and includes at least two piezo-electric ultrasound transceivers;
a second sensor array that is attached to the band, movable relative to and within the band in the circumferential direction of the band, is attached to the band a fixed distance in a longitudinal direction that is perpendicular to the circumferential direction of the band from the first sensor array, and includes at least two piezo-electric ultrasound transceivers;
an electronics module including a first 9-axis motion sensor and a sensor input, the sensor input configured to receive a first signal from the first sensor array and receive a second signal from the second sensor array; and
a second 9-axis motion sensor configured to allow attachment to the trunk of the user near the level of the user's heart; and
a base station, the base station configured to receive sensor data from the electronics module and from the second 9-axis motion sensor, determine a position of the vital sign monitor relative to the second 9-axis motion sensor, and calculate from the received sensor data at least a blood pressure measurement, the calculated blood pressure measurement being based in part on the determined position of the vital sign monitor relative to the second 9-axis motion sensor;

wherein the band is configured to allow placement on an upper arm of a user, and wherein the first and second sensor arrays are moveable in the circumferential direction within the band to enable each to be positioned above the brachial artery of the user.

18. The remote vital sign monitoring system of claim 17, wherein the ultrasound frequency produced by each of the piezo-electric ultrasound sensors in the first array of sensors is between 3 MHz and 7 MHz.

19. The remote vital sign monitoring system of claim 17, wherein the piezo-electric ultrasound transceivers each include:
- a transmitter, wherein the transmitter includes: a first electrical connection; and a second electrical connection;
- a receiver, wherein the receiver includes: a first electrical connection; and a second electrical connection; and
- an isolation region, wherein the isolation region separates the transmitter and the receiver.

20. The remote vital sign monitoring system of claim 17, wherein the band defines a circumference, the band further comprising a first slot in which the first sensor array is disposed and a second slot in which the second sensor array is disposed, the first and second slots being oriented along the circumference of the band and being configured to allow the first and second sensor arrays to move independently and circumferentially about the band by way of movement within the first and second slots to thereby enable positioning of the first and second sensor arrays over the brachial artery of the user when the band is placed on the upper arm of the user.

* * * * *